United States Patent [19]

Loo

[11] 4,452,068

[45] Jun. 5, 1984

[54] GROOVED IMPACTOR AND INERTIAL TRAP FOR SAMPLING INHALABLE PARTICULATE MATTER

[75] Inventor: Billy W. Loo, Oakland, Calif.

[73] Assignee: The United States of America as represented by the United States Department of Energy, Washington, D.C.

[21] Appl. No.: 351,389

[22] Filed: Feb. 23, 1982

[51] Int. Cl.³ .......................................... G01N 15/02
[52] U.S. Cl. ............................................................ 73/28
[58] Field of Search ................ 73/28, 432 PS, 863.22; 55/270

[56] References Cited

U.S. PATENT DOCUMENTS

| | | | |
|---|---|---|---|
| 555,553 | 3/1896 | Austin | 55/423 |
| 1,519,428 | 12/1924 | Wilisch | 55/234 |
| 3,252,323 | 5/1966 | Torgeson | 73/28 |
| 3,623,828 | 11/1971 | Shapiro | 417/2 |
| 3,795,135 | 3/1974 | Andersen | 73/28 |
| 4,133,202 | 1/1979 | Marple | 73/28 |
| 4,255,172 | 3/1981 | Smith | 55/270 |
| 4,275,566 | 6/1981 | Bonn | 417/901 |
| 4,279,156 | 7/1981 | Bell | 73/863.22 |

OTHER PUBLICATIONS

Benjamin Y. H. Liu et al., "Aerosol Sampling Inlets and Inhalable Particles", Particle Technology Lab. Pub. No. 397, Oct. 1979.

Primary Examiner—Stephen A. Kreitman
Attorney, Agent, or Firm—L. E. Carnahan; Roger S. Gaither; Michael F. Esposito

[57] ABSTRACT

An inertial trap and grooved impactor for providing a sharp cutoff for particles over 15 microns from entering an inhalable particulate sampler. The impactor head has a tapered surface and is provided with V-shaped grooves. The tapered surface functions for reducing particle blow-off or reentrainment while the grooves prevent particle bounce. Water droplets and any resuspended material over the 15 micron size are collected by the inertial trap and deposited in a reservoir associated with the impactor.

12 Claims, 3 Drawing Figures

GROOVED IMPACTOR AND INERTIAL TRAP FOR SAMPLING INHALABLE PARTICULATE MATTER

BACKGROUND OF THE INVENTION

The invention described herein arose at the Lawrence Berkeley Laboratory under Contract No. W-7405-ENG-48 between the United States Department of Energy and the University of California.

The invention relates to air pollution monitoring, particularly to apparatus for collecting air samples, and, more particularly, to an inertial trap and a grooved impactor for sampling inhalable particulate matter.

In many cases where air pollution is monitored, it is desired to collect only the pollutants likely to cause harm to people. Since people normally have a built-in filter system that prevents airborne particles larger than 15 micrometers from reaching the respiratory system, it is necessary to remove all such larger particles if an accurate sampling of potentially harmful particulate matter is to be collected.

Particulate samplers of various types are known in the art as exemplified by U.S. Pat. No. 3,252,323, issued May 24, 1966, to W. L. Torgeson; U.S. Pat. No. 3,795,135, issued Mar. 5, 1974, to A. A. Anderson; U.S. Pat. No. 4,133,202, issued Jan. 9, 1979, to V. A. Marple; and U.S. Pat. No. 4,255,172, issued Mar. 10, 1981, to M. L. Smith. In addition, co-pending U.S. Application Ser. No. 134,351 filed Mar. 27, 1980, now U.S. Pat. No. 4,301,022 issued Nov. 17, 1981, describes and claims a high efficiency virtual impactor for dividing a particle-containing gas flow into coarse and fine particle-containing flows for particle collection. Further, an inertial impactor utilizing a simple cup impactor is described in an article by B. Y. H. Liu et al entitled "Aerosol Sampling Inlets and Inhalable Particles", Particle Technology Laboratory Publication No. 397, University of Minnesota, Minneapolis, Minn., October 1979.

Problems associated with the prior known particle sampling apparatus relate to particle bounce, reentrainment, and the accumulation of debris or water which may affect the critical geometry in the impaction region, such that particles larger than those desired (15 m) are not reentrained in the smaller particle flow. Thus, a need recognized in the art, is a method or apparatus for reducing or eliminating particle bounce and associated reentrainment thereof. Various prior art apparatus have been directed to separating material by use of curved members, ridged or angled members, etc., which function to slow the flow of the material during separation thereof. Such is exemplified by U.S. Pat. No. 555,553, issued Mar. 3, 1896, to E. Austin; U.S. Pat. No. 1,519,428, issued Dec. 16, 1924, to J. A. Wilisch; U.S. Pat. No. 3,623,828, issued Nov. 30, 1971, to H. Shapiro; and U.S. Pat. No. 4,275,566, issued June 30,, 1981, to J. W. Bonn. While the prior known apparatus have been effective in producing the desired results, none has provided a solution to the above-described problem associated with particle bounce, reentrainment, etc., in air monitoring and sampling apparatus.

Therefore, it is an object of this invention to provide a particulate sampling apparatus which substantially eliminates the problems associated with particle bounce and reentrainment.

A further object of the invention is to provide a particulate sampling device which includes an inertial trap and impactor.

Another object of the invention is to provide an apparatus for sampling airborne particles which will provide a sharp transmission efficiency particle cutoff at 15 micrometers (or other particle size cut desired).

Another object of the invention is to provide an inertial trap and impactor for inhalable particulate matter which utilizes a tapered and grooved impactor head for preventing particle bounce and particle reentrainment.

Other objects of the invention will become apparent to these skilled in the art in view of the following description and accompanying drawings.

SUMMARY OF THE INVENTION

The present invention provides a solution to the above-referenced problems associated with particle bounce, reentrainment, etc., in a particulate-sampling apparatus. This is accomplished by utilizing a sampling apparatus having an inertial trap and impactor which provides the desired sharp cutoff for particles over 15 microns, wherein the impactor head has a tapered upper surface provided with V-shaped grooves. The grooves prevent or substantially eliminate particle bounce, and any particle blow-off or reentrainment is intercepted by the inertial trap and directed into a partitioned reservoir.

More particularly, the present invention provides an inhalable paticulate sampler with a 15-micron cutoff and a flow rate of about 1 $m^3$/hr. The particle bounce by a single backscattering of very elastic spherical particles is eliminated by covering the impactor head with concentric V-shaped grooves with opening angles of less than 90°. Backscattering through double and tripple bounces are also suppressed if the opening angles of the grooves are designed to be under 45° and 30° respectively. A practical 15 $\mu$m cutpoint design calls for grooves about 1.27 mm wide with an opening angle of 35° and forming concentric rings on a 5° taper or slope on the impactor head from the center outwardly. The impactor is fully shielded from the external wind by a cover arrangement. The downward slope of the impactor head helps to direct any water and loose material into the peripheral inertial trap and eventually into a reservoir therebelow.

DETAILED DESCRIPTION OF THE INVENTION

The invention is directed to an inertial trap and impactor for inhalable particulate inlets of a particle size separator having a particulate inlet with a 15-micron cutoff and capable of operation with a flow rate of 1 $m^3$/hr, for example. A compact impactor cup is used to achieve a sharp cutoff with minimal wall loss and disturbance due to the local wind trajectories. An inertial trap and a partitioned reservoir are used to arrest particle bounce, reentrainment and collect water, etc. The worst case of particle bounce by backscattering of very elastic spherical particles is limited to under 2% by covering the impactor head with concentric V-shaped grooves with opening angles of about 35°. The impactor head is provided with a taper or downward slope of about 5°, for example, which helps to direct any water and loose material into the peripheral inertial trap and eventually into a reservoir having a volume of 60 ml, for example.

Figure 1:
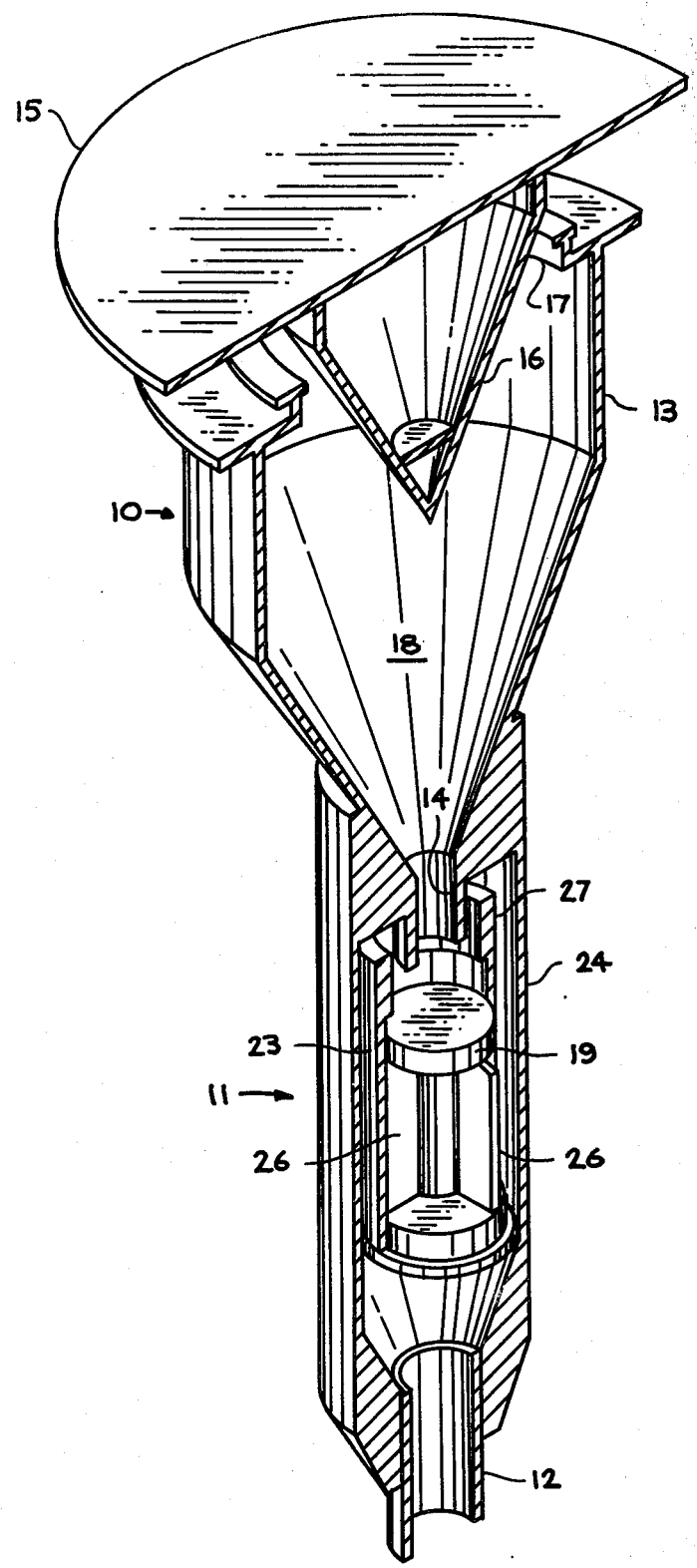
FIG. 1 is a cut-away view of an embodiment of a portion of an inhalable particulate sampler utilizing the inertial trap and impactor of the invention.
Figure 2:
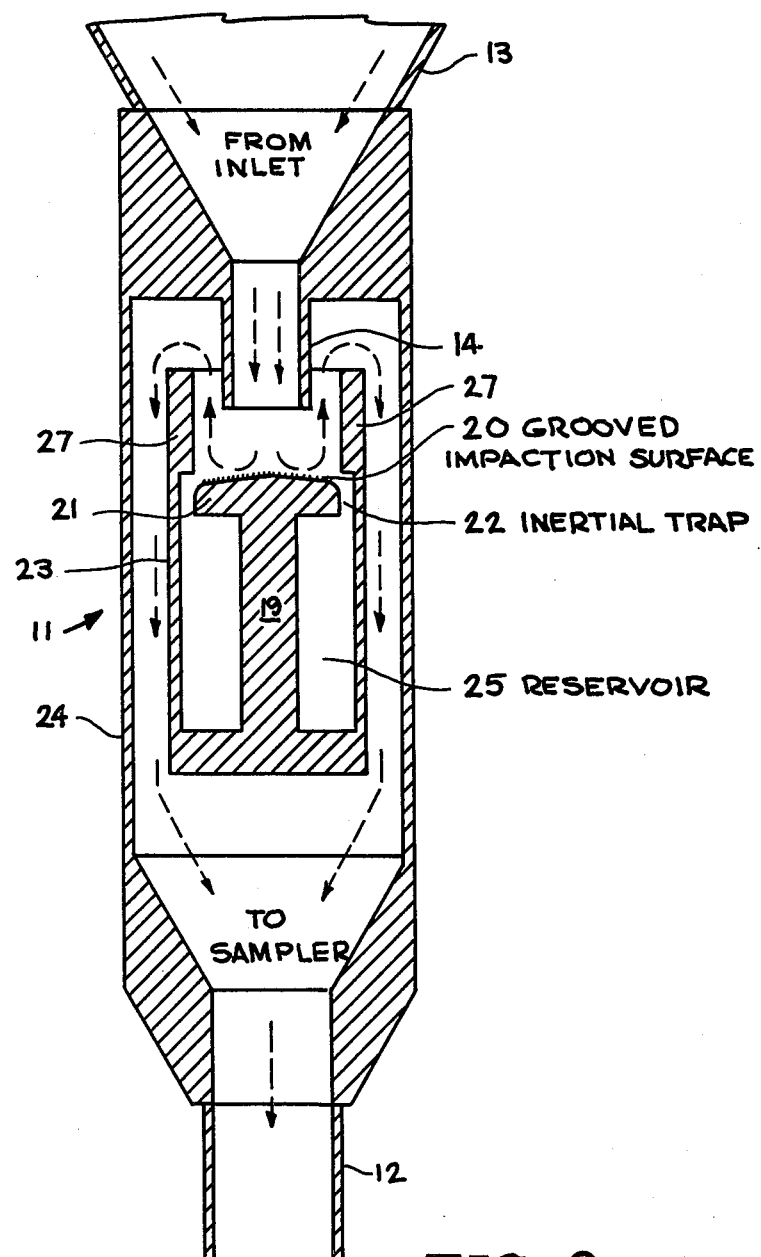
FIG. 2 illustrates an enlarged cross section of the particle size separator of the FIG. 1 sampler mechanism.
Figure 3:
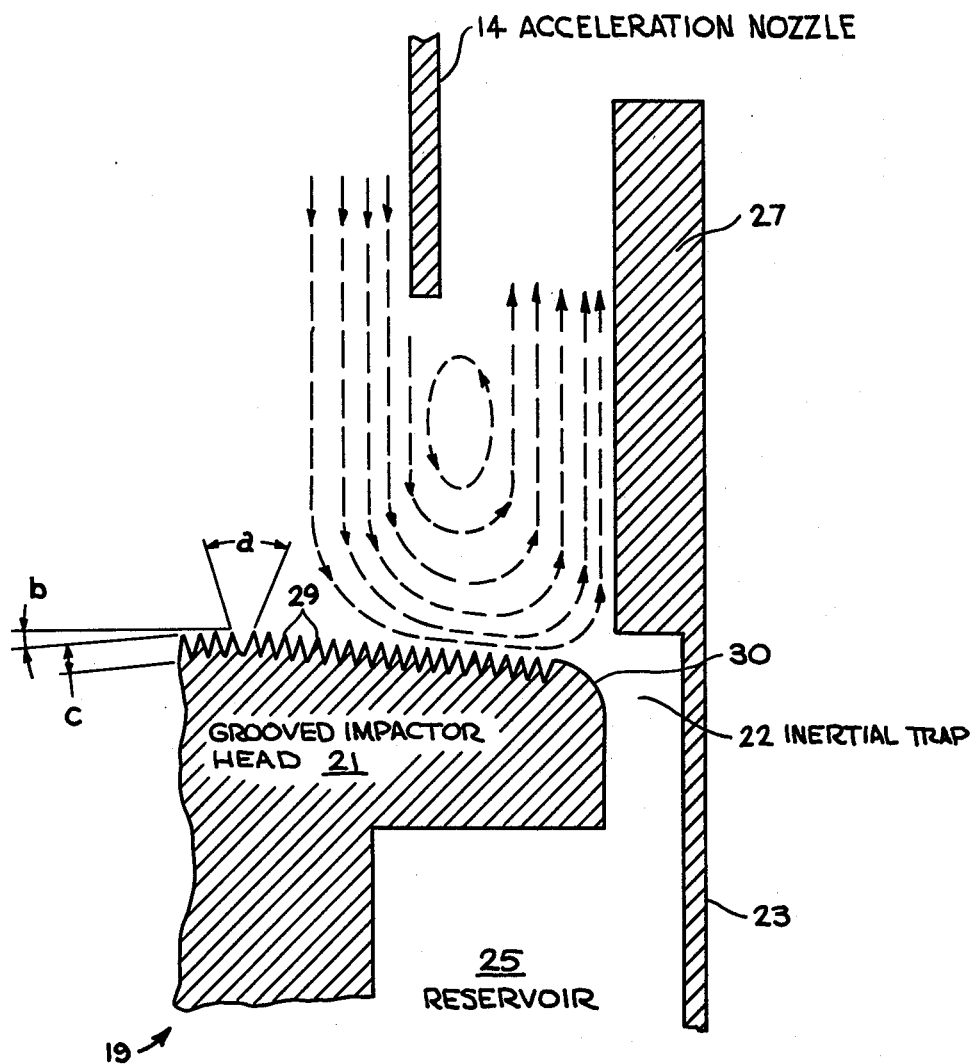
FIG. 3 illustrates a further enlarged section of the impactor and inertial trap of FIG. 2, made in accordance with the invention.

Referring now to the drawings, FIG. 1 shows a cutaway of an upper portion of an inhalable paticulate sampler utilizing a particle-size separator, shown in greater detail in FIG. 2, which incorporates the inertial trap and impactor arrangement of the present invention, shown in detail in FIG. 3.

The illustrated portion of the inhalable particulate sampler of FIG. 1 basically comprises an inlet section generally indicated at 10, and a particle-size separator section generally indicated at 11 which is adapted to be attached via connection 12 to detection and monitoring mechanism, not shown. The inlet section 10 basically consists of a funnel-shaped assembly 13 terminating in an acceleration nozzle 14, and a cover assembly 15 is positioned on and secured to funnel-shaped assembly 13 through which air to be monitored passes into particle-size separator section 11. The air enters through an annular slit between a deflection cone 16 and a guard-ring 17 of the cover assembly 15 which helps to make the inlet section 10 more weatherproof by stopping runovers from rain splashes. Variations in efficiency as a function of wind speed have been reduced by deflecting the incoming air stream by the deflection cone into a deceleration chamber 18 formed by funnel-shaped assembly 13. The stagnated air is then passed through nozzle 14 onto an impactor 19 of the particle-size separator section 11.

FIG. 2 illustrates the particle-size separator section 11 and the air flow therethrough. The air from inlet section 10 is drawn through acceleration nozzle 14 and directed onto an upper surface 20 of a head 21 of impactor 19, head 21 having a slightly conical configuration produced by a downward or outward slope of 5°, for example, as illustrated in FIG. 3. The downward slope of the upper surface of impactor head 21 may vary from 2° to 8° and helps to direct any water and loose material into a peripheral inertial trap 22 formed by a space itermediate impactor head 21 and a wall-forming member 23 positioned within an outer tubing or housing 24. Material passing into trap 22 is collected in a reservoir 25 which may have a volume of 60 ml, for example. Any angular momentum in the incoming air jet or asymmetry in the radial flow at the impactor surface 20 tends to cause some streamlines to make a spiral excursion into the reservoir 25 and deposit particles unintentionally. Such penetration of streamlines into the reservoir reduces the sharpness of the impactor transmission curve. To minimize this undesired effect, four (4) partition vanes 26 (only two shown in FIG. 1) are secured in reservoir 25 between impactor 19 and wall-forming member 23 to divide reservoir 25 into four (4) sections. Wall-forming member 23 includes an upper section 27 of greater thickness which is located with respect to impactor head 21 so as to define the desired entrance distance or mouth width of inertial trap 22. The folded air flow geometry in the particle size separator section 11, as indicated by the flow arrows in FIG. 2, gives rise to a compact external body which minimizes the interference by the inlet section 10 on the oncoming wind trajectories.

An important objective of the particle-size separator section 11 is the ability to perform reliable, unattended sampling in the field for an extended period. For example, many sampling devices use impactors which employ various techniques for coating the impactor surface with a sticky substance to prevent particle bounce. Particle bounce at the impactor head can be classified into two categories depending on whether the exit angle of the particle with respect to the streamlines near the surface is large or small. As can be seen in FIG. 3, if a large particle does not adhere to the impactor head it tends to be swept radially outwards by the surface streamlines, indicated by the directional arrows, such that the particle is swept through the inertial trap and deposited in the reservoir where it is never subject to further reentrainment. The same process applies to any debris or loose deposition on the surface of the impactor head. However, if a very symmetrical bouncy particle or substance makes a near 180° vertical bounce of several milimeters (mm) after hitting a hard, substantially flat, impaction surface, it has a chance to be carried by the upper streamlines into the flow of small (less than 15 $\mu$m) particles. The present invention eliminates this type of particle bounce or backscattering.

As more clearly illustrated in FIG. 3, the upper surface 20 of impactor head 21 is provided with concentric V-shaped grooves 29 having an opening angle indicated at a of about 35°. If the opening angle of the grooves 29 is less than 90° then an incoming particle in the vertical direction must scatter forward into a groove. Similarly, opening angles of less than 45° and 30° will prevent secondary and tertiary back scattering. Due to the grooved surface 20, there is little flat surface oriented for large-angle backscatter; and when the grooves 29 are filled with ambient aerosol, the particle impact tends to be inelastic. Resuspended material which tends not to have a high vertical velocity component will be swept radially outwardly by the surface streamlines and thus be caught efficiently by the inertial trap 22. In the embodiment illustrated in FIG. 3, the grooves 29 have opening angles a of 35° with a depth indicated at c of 2.0 mm, the downward slope indicated at b of impactor head surface 20 being 5°. Note that the outer upper periphery of impactor head 21 is curved, as indicated, at 30 to increase the efficiency of the inertial trap 22. The performance is independent of groove size and angle, provided that the groove opening angle is about an order of magnitude smaller than the characteristic diameter of the associated air jet through nozzle 14 so as not to affect the original flow characteristics.

Various tests have been conducted which establish that there is a significant reduction in particle bounce when an impactor head is provided with grooves in accordance with the present invention. For example, in tests using symmetrical bouncy particles, the total particle bounce of the grooved impactor was reduced to less than 2% of the bounce of a flat (nongrooved) impactor. For further desciption of the tests, attention is directed to report LBL-11682 entitled "A New Inhalable Particulate Impactor with Inertial Trap", bearing a date of January 1981, by Billy W. Loo et al, Lawrence Berkeley Laboratory, Berkeley, Calif., said report being incorporated herein by reference.

It has thus been shown that the present invention provides a compact inertial size separator having a sharp particle size cut-off for sampling or monitoring apparatus. Through the use of the inertial trap and grooved impaction surface, traditional problems of particle bounce and reentrainment have been virtually eliminated. An inherent advantage of the inertial trap is that bounce-off or blow-off particles are immediately removed from the air flow region so that resuspension of these materials after prolonged field operation will not be possible.

Since the size separator using inertial trap and grooved impactor of this invention is based on the well-understood theory of jet impaction, the various features described above can be generalized readily to other situations where different flow rates and cutoff points are called for. The apparatus utilizing the inertial trap and grooved impactor is designed for quick disassembling for field service and to provide an inhalable particle sampler with a reliable weatherproof inlet. Thus, the present invention overcomes the problems of the prior known particle-size samplers, thus substantially advancing the state of this art.

While a particular embodiment of the invention has been illustrated and/or described, modifications will become apparent to those skilled in the art, and it is intended to cover in the appended claims all such modifications as come within the scope of this invention.

I claim:

1. In an inhalable particulate sampler having at least an inlet section and a particle-size separator section, the improvement comprising: means for substantially preventing particle bounce and reentrainment of particles over a selected maximum size, comprising a particle impactor, said impactor being provided with a surface onto which substantially all incoming particles are initially directed, said impactor surface having a plurality of V-shaped grooves thereon, and means which includes said particle impactor for forming an inertial trap adjacent a peripheral area of said particle impactor whereby particles greater than a selected maximum size are trapped by said inertial trap.

2. The improvement of claim 1, wherein said grooves on the surface of said particle impactor are concentric and have an opening angle of not greater than 90°.

3. The improvement of claim 1 or 2, wherein said surface of particle impactor has an outwardly and downwardly slope in the range of about 2° to 8°.

4. The improvement of claim 3, wherein said grooves have an opening angle of about 35° and a depth of about 2.0 mm.

5. The improvement of claim 1, wherein said particle impactor consists of an impactor member having an impactor head on which said grooved surface is located, said grooves being of a concentric configuration having an opening angle or not greater than 90°.

6. The improvement of claim 1, additionally including a reservoir in open communication with said inertial trap defining means for collecting at least said particles having a size greater than said maximum size, said reservoir being provided with a plurality of partitions for preventing spiral excursions of flow streamlines into said reservoir and the resultant depositing in said reservoir of undesired particles.

7. A method for substantially eliminating particle bounce and reentrainment of particles over a maximum size in a particulate-collecting apparatus, comprising the steps of: providing a particle impactor onto which substantially all incoming particles are directed, providing the particle impactor with an outwardly and downwardly sloping upper surface, providing the upper surface of the particle impactor with a plurality of V-shaped grooves having an opening angle not greater than about 90°, and forming an inertial trap about the periphery of the particle impactor, such that particles over a maximum size are directed into the inertial trap by the grooved upper surface of the particle impactor.

8. The method of claim 7, additionally including the step of providing a partitioned reservoir in communication with the inertial trap for collecting the particles passing through the trap.

9. The method of claim 7, wherein the V-shaped grooves are provided by forming same to define a groove width constituting approximately an order of magnitude smaller than the characteristic diameter of an air jet through an associated nozzle directed onto the grooves.

10. An improved particle impactor for an inhalable particulate sampler apparatus comprising: a downwardly and outwardly sloping upper surface onto which substantially all incoming particles are directed, and a plurality of concentric grooves on said upper surface, whereby vertical bounce of particles of a selected maximum size striking said upper surface of said particle impactor is substanially reduced.

11. The improved particle impactor of claim 10, wherein said concentric grooves are of a V-shaped configuration with an opening angle of not greater than 35°.

12. The improved particle impactor of claim 11, wherein said upper surface of said impactor has a slope in the range of 2° to 8°.

* * * * *